United States Patent
Ioualalen et al.

(10) Patent No.: US 9,192,679 B2
(45) Date of Patent: *Nov. 24, 2015

(54) GALENICAL SYSTEM FOR ACTIVE TRANSPORT, METHOD FOR PREPARATION AND USE

(71) Applicant: Capsugel France SAS, Colmar (FR)

(72) Inventors: Karim Ioualalen, Saint-Orens-de-Gameville (FR); Rosanne Raynal, Saint-Orens-de-Gameville (FR)

(73) Assignee: Capsugel France SAS, Colmar (FR)

( * ) Notice: Subject to any disclaimer, the term of this patent is extended or adjusted under 35 U.S.C. 154(b) by 0 days.

This patent is subject to a terminal disclaimer.

(21) Appl. No.: 14/523,999

(22) Filed: Oct. 27, 2014

(65) Prior Publication Data

US 2015/0044297 A1    Feb. 12, 2015

Related U.S. Application Data

(63) Continuation of application No. 12/767,248, filed on Apr. 26, 2010, now Pat. No. 8,911,788, which is a continuation of application No. 10/550,027, filed as application No. PCT/FR2004/000729 on Mar. 24, 2004, now abandoned.

(30) Foreign Application Priority Data

Mar. 24, 2003  (FR) ..................................... 03 03568

(51) Int. Cl.
| | | |
|---|---|---|
| *A61K 9/50* | (2006.01) | |
| *A61K 9/14* | (2006.01) | |
| *A61K 47/44* | (2006.01) | |
| *A61K 9/16* | (2006.01) | |
| *A61K 31/167* | (2006.01) | |
| *A61K 31/65* | (2006.01) | |
| *A61K 31/7048* | (2006.01) | |
| *A61K 47/12* | (2006.01) | |
| *A61K 9/00* | (2006.01) | |

(52) U.S. Cl.
CPC . *A61K 47/44* (2013.01); *A61K 9/14* (2013.01); *A61K 9/1617* (2013.01); *A61K 31/167* (2013.01); *A61K 31/65* (2013.01); *A61K 31/7048* (2013.01); *A61K 47/12* (2013.01); *A61K 9/0095* (2013.01)

(58) Field of Classification Search
None
See application file for complete search history.

(56) References Cited

U.S. PATENT DOCUMENTS

| | | | | |
|---|---|---|---|---|
| 4,590,062 A | * | 5/1986 | Jang | 424/469 |
| 6,572,892 B1 | * | 6/2003 | Ioualalen et al. | 424/489 |
| 8,911,788 B2 | * | 12/2014 | Ioualalen et al. | 424/502 |

* cited by examiner

*Primary Examiner* — Jeffrey T Palenik
(74) *Attorney, Agent, or Firm* — Klarquist Sparkman, LLP

(57) ABSTRACT

The invention relates to a novel galenical system for taste masking, protecting an active substance, in particular in an acid medium, modulating releasing properties, masking mucous irritability and toxicity of certain active substances, for preparing aqueous forms which have a masked taste, are stable and pH independent. Said invention also relates, in particular to a galenical system which is embodied in the form of lipidic solid particles and strictly hydrophobic and devoid of water, surface active agents, emulsifiers, solvent traces and which is characterized in that it comprises at least one type of hydrophobic wax and at least one type of fatty non-neutralised acid.

19 Claims, No Drawings

GALENICAL SYSTEM FOR ACTIVE TRANSPORT, METHOD FOR PREPARATION AND USE

This is a continuation of U.S. application Ser. No. 12/767,248, filed Apr. 26, 2010(pending), which is a continuation of U.S. application Ser. No. 10/550,027, filed Dec. 22, 2006 (abandoned) which is a 371 filing of International Application No. PCT/FR2004/000729, filed Mar.24, 2004, all of which are incorporated herein by reference.

This invention relates to a new galenic system for the protection of an active constituent, particularly a medicine, against degradation during transit in the stomach following oral absorption.

The galenic system according to the invention also enables masking of the taste of an active constituent in the galenic system, if any, stabilisation of the said active constituent, modulation of the release properties of the said active constituent, masking or mucosal irritability effects and toxicity of some active constituents.

The simplest and the most practical therapeutic administration path is oral. In France, this path is used for 75% of all medicines taken (Pharmacie galénique, A. Le Hir—Editions Masson). Galenic forms intended to be taken orally are essentially in two forms, liquid and dry. They have the enormous advantage that they do not require any medical treatment when taking medicine.

The pH of the stomach is between 2 and 6. The acid nature of the stomach environment can cause degradation of active constituents contained in ingested compositions before they have reached the intestine, where theoretically they are absorbed through the intestinal mucous membrane to pass into the circulation. Such a deleterious stomach transit effect could be contradictory to the objective, namely absorption of the said active constituent by the organism in the most efficient form for the required effect. This disadvantage is particularly important for pharmaceutical compositions.

Therefore there is a need for an excipient for active constituents ingested orally, capable of assuring stomach transit for the said active constituent without degrading the said active constituent. This is one of the purposes of this invention.

Other problems are well known, with galenic forms intended to be taken orally, particularly galenic forms for medical purposes. A recurrent problem with these galenic forms is compliance.

Compliance is a capital factor that directly depends on the efficiency of the therapeutic treatment. Compliance, or correct use of the medicine, is defined as being the action of following a medical treatment in accordance with the indications in the prescription; respecting the treatment duration, the number of times and the times during the day that the medicine is taken. A medicine may be inactive or not very efficient if is not taken at a sufficient dose or sufficiently frequently. For intermittent disorders, failure of correct compliance of the treatment can only delay the cure and lead to relapses, sometimes responsible for serious complications. Poor compliance in the case of chronic diseases can cause irreversible damages.

The main difficulties encountered during oral administration vary depending on the presentation.

The disadvantages for dry forms, tablets, capsules, gelatine capsules are deglutition and taste. Some populations such as the elderly, children and some persons with mental disorders must choose the liquid form.

It is very easy to take medicine in liquid form, but this form always faces the unsolved problems of concealing the taste and instability of many active constituents in the aqueous phase.

Another of the objectives of this invention is to propose a galenic system capable of efficiently concealing the taste.

Finally, regardless of the form, irritability, mucosal toxicity and gastro-toxicity problems are also encountered when taking some active constituents, particularly medicines such as anti-inflammatory medicines.

Another purpose of this invention is to propose a galenic system capable of a delayed release of an active constituent, particularly so that it is not released into stomach during ingestion. This property requires the use of a galenic system stable in an acid medium, in other words resistant to an acid pH.

As mentioned in document PCT/US99/27981, page 2, line 4, methods used to minimise bad taste are varied, including the addition of sweeteners, aromas, effervescent formulation and coating technologies. Coating techniques provide the only means of concealing the taste, while other approaches attempt to make the nature of the preparation more appetising. These coating techniques were also selected to prevent the release of gastrotoxic active constituents into the stomach.

Coating techniques consist of putting a layer of isolating compounds, polymers and mixes into place around the active constituent to isolate it from the external environment. Many natural and synthetic polymer compounds have been used to build up this external layer. They include mainly cellulose derivatives such as hydroxypropylmethylcellulose (HPCM), ethylcellulose, carboxymethylcelluloses, hydroxypropylmethylcellulose phthalate or mixes of these products. This technique has given interesting results for varying the release rate and for gastroprotection, but those skilled in the art know that the taste is not concealed satisfactorily and the formulation in water remains unstable in time, which is incompatible with the preparation of aqueous forms such as syrups and suspensions.

Other polymers such as polyacrylate derivatives, amoniomethacrylate polymers or methacrylate proposed by the RÔHM Company have been used, as described in document FR 2795962 and WO 98/47493. A lot of work has been carried out with starch and particularly polycarbophiles and Carbopol as described in patent WO 02/092106.

These coating techniques are well known to those skilled in the art. A distinction can be made between physical coating processes based on sprinkling of the coating solution in a turbine or in a fluidised bed as described in patents WO 00/30617 and WO 02/092106 firstly, and secondly physicochemical coating based on coacervation or the separation of phases as described in patent U.S. Pat. No. 3,341,416. All these techniques lead to setting up one or several external polymeric layers covering a central particle composed of the pure active constituent or a mix in the form of granules of active constituents with other support materials as described in document EP 1194125 issued by the Prographarm Company.

We have seen that it was impossible to conceal the taste and keep absorption properties of the initial molecule at the same time.

Immediate release at the digestive tube depends on the use of a dependent pH polymer very sensitive to a pH greater than 7 in the mouth cavity or the stomach, which requires the addition of acid into the final formulation.

These coating techniques have a number of disadvantages: gastroprotection is not complete the taste is not completely concealed and the taste of compounds that are very bitter is still too unpleasant release rates are modified coating particles have a size of a few hundred microns and are perceptible during absorption. In this case, rupture of the particles can cause a bad taste coating processes are complex, they include many steps and are expensive.

These technologies are not compatible with preparation of syrups that are stable in the long term.

Therefore these technologies are not fully satisfactory.

The inventors have demonstrated that, surprisingly and unexpectedly, the addition of non-neutralised fatty acids to the compositions of solid lipidic particles prepared according to the process described in patent WO 99/65448 that can contain an active constituent, provides a means of obtaining stable hydrophobic particles in the stomach and that are released only in the digestive tube, thus providing gastroprotection and complete concealing of the taste without modifying the release properties of the active constituent.

Thus, this invention proposes a new galenic system enabling:
gastroprotection,
concealing the taste,
protection of the active constituent, particularly in an acid environment,
the possibility of modulating release properties,
concealing of mucosal irritability effects and toxicity of some active constituents,
the preparation of aqueous forms with a concealed taste, stable and with independent pH.

The galenic system according to the invention is characterised in that it is composed of a mix of hydrophobic compounds insoluble in water, in that it is in solid form at ambient temperature and that it has absolutely no surfactant compounds, solvent residues or water that could cause hydrolysis or oxidation reactions of an active constituent containing it. This galenic system has the capability of incorporating hydrophilic, hydrophobic or mineral type compounds.

Thus, the purpose of the invention is a strictly hydrophobic galenic system in the form of solid lipidic particles, containing no water or surfactants, or emulsifying agents or traces of solvents, characterised in that it comprises at least one hydrophobic wax and at least one non-neutralised fatty acid.

In the remainder of the text, the terms "galenic system", "lipidic particle" and even "droplet" or "lipidic droplet" will be understood as having the same meaning.

In one particular form of the invention, the galenic system is also talc free.

According to another particular form of the invention, the lipidic particles are solid at a temperature of up to 45° C. and preferably up to 37.5° C.

According to another particular form of the invention, the lipidic particles are in spherical form.

A hydrophobic wax according to the invention means that the galenic system may be composed of one or several vegetal, animal or mineral waxes, or a mix of one or several waxes and at least one non-amphiphilic oil.

The galenic system may also comprise at least one hydrophobic compound capable of adjusting the melting point and the physicochemical properties such as the hardness. Examples of hydrophobic compounds include beeswax and palm oil.

An appropriate composition compatible in terms of toxicity, biocompatibility, non-immunogenicity and biodegradability with absorption by mouth or any other administration method, should be chosen. In this case, the compounds will be chosen from among compounds already used for oral administration such as those defined in the GRAS list published by the Food and Drug Administration, such that the particles formed maintain their incorporation, taste concealing and stabilization properties for active constituents.

Thus according to the invention, the wax may be chosen from among any known wax compatible with the requirements of the invention. In particular, the wax may be chosen from among:
triglycerides and derivatives
palm oil
Carnauba wax,
Candellila wax
Alfa wax
cocoa butter
ozokerite
vegetal waxes such as olive wax, rice wax, hydrogenated jojoba wax or absolute flower waxes
beeswaxes and modified beeswaxes.

According to one particular form of the invention, the wax may be a mix of waxes.

According to the invention, a wax or a mix of waxes with a melting point of between 15° C. and 75° C., and preferably between 30° C. and 45° C. can be used.

According to the invention, the quantity of wax may be between 0.5% and 99%, and preferably between 1% and 50%.

According to the invention, the non-neutralised fatty acid may be any non-neutralised fatty acid compatible with the requirements of the invention. The non-neutralised fatty acid may be chosen from among fatty acids with linear chains with between 4 and 18 carbon atoms, for example such as myristic acid, lauric acid, palmitic acid or oleic acid.

According to one particular form of the invention, the non-neutralised fatty acid may be composed of a mix of non-neutralised fatty acids.

According to the invention, the non-neutralised fatty acid may be used with a fatty acid content by mass of between 0.5% and 75% and preferably between 1% and 30%.

The galenic system according to the invention may also contain oily, pasty or solid additives, liposoluble or hydrosoluble active ingredients.

Other compounds can also be used, such as fatty alcohols with a high molecular weight, preferably linear and saturated fatty acids with an even number of carbon atoms between 12 and 30, acid and alcohol esters with a high molecular weight and particularly esters of linear and saturated acids with an even number of carbon atoms between 4 to 20, and linear and saturated alcohols with an even number of carbon atoms between 14 and 32. In all cases, the mix obtained must be characterised by a final melting point between 15° C. and 75° C., by the absence of surfactant compounds, a hydrophobic behaviour and non-wettability by water. Apart from the waxes mentioned above, the composition according to the invention may contain an oil or a mix from among:
hydrophobic silicon oils with a viscosity between 5 and 9000 centistockes, cyclomethicones,
lipophile organofluoridic oils,
perhydrosqualene.

Other oily compounds such as oleic alcohol, lanoline, sunflower oil, palm oil, olive oil, fatty acids and fatty alcohols may be used, but the oily mix obtained must be characterised by a hydrophobic behaviour, a lack of miscibility with water and a melting point between 15° C. and 75° C., and preferably between 30° C. and 45° C.

Clays or oily dispersions of clays, phenyl silicon gums, starches and fatty body structuring agents, can be added into the composition to adjust the consistency.

A number of compounds such as mineral fillers can be added to the hydrophobic matrix of the galenic system, to modulate the density and plasticity. Talc and kaolin will advantageously be chosen for the mineral compounds.

The size of lipidic particles according to the invention may be between 0.5 microns and 1500 microns, and preferably between 10 microns and 250 microns.

Lipidic particles according to the invention have the advantage that they can enable delayed release of an active constituent contained in them, very good stability to an acid pH particularly in an acid aqueous formulation, thus enabling protection of the active constituent when they are in contact with an environment with an acid pH, for example such as the gastric environment, and complete concealing of the taste.

Another purpose of the invention is a galenic system according to the invention also comprising an active constituent.

In this description, the term active constituent is used to denote any substances that can be used in cosmetics, pharmacy, biotechnology, in the veterinary field or in food. In particular, according to the invention, the active constituent may be an active therapeutic substance that can advantageously be administered to man or other animals to diagnose, cure, reduce, treat or prevent a disease.

According to the invention, the active constituent may be any hydrophilic, hydrophobic or mineral compound.

According to the invention, the active constituent may be dissolved or dispersed in the galenic system.

Obviously, according to the invention, the active constituent may be a mix of active constituents.

The active constituent may be chosen from among essential oils, aromas, pigments, fillers, colouring agents, enzymes and coenzymes and other active substances.

Active constituents that may be incorporated into the galenic system according to the invention include vitamins or provitamins A, B, C, D, E, PP and their esters, carotenoids, anti-radical substances, hydroxyacids, antiseptics, and molecules acting on the pigmentation, inflammation, biological extracts.

The active constituent may also be chosen from among preservatives, antioxidants, colouring agents and pigments, cells and cellular organites or pharmaceutical compounds intended for the treatment of pathologies, particularly skin or mucosal pathologies.

Examples of therapeutic active constituents that could be incorporated into the galenic system according to the invention include antibiotics, antifungicides, antiparasites, antimalaria agents, adsorbents, hormones and derivatives, nicotine, antihistamines, steroidal and non-steroidal anti-inflammatory agents, antiallergic agents, antalgics, local anaesthetics, antivirals, antibodies and molecules acting on the immunitary system, cytostatics and anticancer agents, antalgics, hypolipemiants, vasodilators, vasoconstrictors, inhibitors of the angiotensin and phosphodiesterase conversion enzyme, nitrated and antianginal derivatives, beta-blocking agents, calcium inhibitors, antidiuretics and diuretics, bronchodilators, opiates and derivatives, barbiturates, benzodiazepines, molecules acting on the central nervous system, nucleic acids, peptides, anthracenic compounds, paraffin oil, polyethylene glycol, mineral salts, antispasmodic agents, gastric antisecretion agents, clay and polyvinylpyrrolidone gastric cytoprotectors, starch. This exhaustive list is in no way limitative.

According to the invention, also comprise an active constituent and have a melting temperature after the active constituent has been incorporated of between 15° C. and 75° C. and preferably between 30° and 45° C.

The capacity of particles for holding an active constituent may vary from 0.02% to 75% by weight of the particles, and particularly from 5 to 50%.

Those skilled in the art know that when these active constituents are incorporated into the galenic system, an appropriate lipidic composition should be chosen such that the particles are solid at the temperature of use with a size preferably between 0.5 microns and 1500 microns and preferably between 0.5 microns and 100 microns, to completely conceal the taste without modifying the release properties and with very good stability in an aqueous formulation even at a high pH. It is also necessary that the process for preparation of the said galenic system also comprising an active constituent can be used.

According to the invention, the galenic system also comprising an active constituent may be prepared using the process described in patent WO 99/65448.

According to this embodiment of the process, the particles are obtained by mixing with moderate heating. More specifically, these compositions are obtained by a process characterised by the fact that wax and oil are mixed at the melting temperature of the wax to obtain a mix characterised by a melting temperature less than the melting temperature of the wax. The initial ratio between the wax and the oil may be modulated so that the melting temperature of the final mix is less than the degradation temperature of the compound to be incorporated that is most sensitive to heat. The final mix must be solid at the temperature of use and in one of these preferred forms it must have a melting point of 37.5° C. The mix is then cooled with appropriate stirring, to a temperature of more than 2° C. or 3° C. at its melting point, to enable inclusion of pharmaceutical active constituents. The mix is then formed to result in hydrophobic spherical particles called particles.

Compared with hot melting techniques, the process according to the invention does not involve any emulsifying agents or amphiphilic products in the composition, to enable stable dispersion during the solidification phase by cooling.

According to one particular embodiment of the process according to the invention, when the active constituent has to be completely eliminated from the surface of lipidic particles, the invention includes a step to wash the said particles obtained with a washing mix including ethanol. In this case, the presence of ethanol in the washing mix is essential to the process since ethanol enables complete washing of any active constituent residues that may be present on the surface of the lipidic particles that could create an unpleasant taste.

Thus according to this particular embodiment of the process according to the invention, the different compounds in the galenic system (including wax and non-neutralised fatty acid) and the active constituent are mixed in a first step of the process. The mix is made hot at 2° C. or 3° C. above the melting point of the compound with the highest melting point. Those skilled in the art know that a stiffing method appropriate to the dispersion of all compounds must be used.

Then in a second step, lipidic droplets are formed comprising the active constituent by dispersing the mix obtained in the first step in a gel prepared with a gelifying, shear thinning and non surface active agent with which the said mix is not miscible, previously adjusted to the same temperature, and with a concentration of gelifying agent between 0.1 g/l and 30 g/l, and preferably between 0.2 g/l and 20 g/l sufficiently high to fix the dispersion.

It may be preferable to inject the composition within the gel, for example through an orifice located at the base of a reaction vessel. Stiffing must be continued throughout injection and has a characteristic of using a blade equipped with an anchor designed to disperse the composition and a second axial blade equipped with a three-vaned impeller designed to for dispersion droplets with the required size. This final step is extremely fast because the droplets are obtained as the composition is being injected. There is no need to maintain stirring after the end of injection, because the droplets are fixed in the gel.

In a third step according to the process, the droplets are immediately cooled to below this mix solidification temperature at the end of the injection and are then washed.

The washing phase is very important because it makes it possible to no longer have any residue on the surface of particles, which could create an unpleasant taste.

Thus, regardless of the form of embodiment of the process according to the invention, particles may be washed using a washing mix composed of water and between 0% and 25% of ethanol.

Finally in a fourth step, the washed particles are then recovered by sieving and are then dried. The particles obtained have excellent size homogeneity and can be manipulated industrially with no special precautions.

Those skilled in the art know that other dispersion methods such as sonication or static mixers can be used.

Therefore the process according to the invention is fast and does not require any long and difficult stirring step. It can incorporate the active constituent into the galenic system during the first mixing step of the different ingredients in the composition.

Examples of shear thinning and non-surface active gelifying agents appropriate for formation of the gel used as the dispersion medium according to the process, include carboxyvinyl polymers such as polyacrylic polymers not modified by hydrophobic groups or surfactants, carrageenans, thickeners and polysaccharidic gels such as xanthenes, guar and carob gums, alginates, cellulose derivatives, pectins, agar or a mix of these products.

Lipidic particles comprising an active constituent may be incorporated into any composition, and particularly into any cosmetic, pharmaceutical, veterinary or food composition.

Another purpose of the invention is a composition comprising at least one lipidic particle containing an active constituent.

The composition according to the invention may also include any additive intended to modify the appearance or the rheology. For example, lubricants can be added to the dry powder of particles to improve their fluidity, for example such as talc, starches, silica powders, antistatic agents. Obviously, the composition according to the invention may be in the form of any appropriate galenic formulation. In one advantageous form of the production, the particles according to the invention are used in aqueous suspensions, syrups and sachets. Finally, the particles may be used in conventional galenic formulations such as capsules, gelatine capsules, granules, oral powders, dispersible powders, tablets, hydrodispersible and orodispersible tablets.

According to another aspect of the invention, the compositions may be used for administration by injection and particularly for the preparation of forms with prolonged release. In this case, lipidic particles according to the invention are prepared so that their size is preferably between 0.5 μm and 5 μm. It is preferable to sieve them to obtain a size distribution conform with the mode of administration. Their waxy composition is chosen to be conform with the requirements for injection. This galenic form can eliminate toxicity problems encountered by polymeric particles obtained using polymerisation in emulsion processes, related to the use of solvents and surfactant compounds.

The particles according to the invention can be used to obtain contents of the active constituent equal to between 0.10 and 2 grams/gram of waxy matrix. Those skilled in the art know that these contents cannot be reached using encapsulation technologies. Finally, particle degradation does not cause any inflammatory reaction like the reaction that can occur with injectable particles based on a polylactic-glycolic polymer.

The following examples are not limitative and are simply used to illustrate the invention. Taste concealing tests for some of the following examples were carried out with a sample of 10 individuals. The results are expressed on the following scale:

1: the taste of the active constituent is detected
2: the taste of the active constituent is perceived slightly
3: the taste of the active constituent is detected
4: the taste of the active constituent is still acceptable
5: the taste of the active constituent is not acceptable.

EXAMPLE 1

Particles Containing Erythromycin

Example given for the production of 120 g of particles containing erythromycin:
Composition:

| | |
|---|---|
| Palm oil | 80 g |
| Oleic acid | 5 g |
| Stearic acid | 4 g |
| Trilaurin | 1 g |
| Erythromycin | 30 g | namely 120 g of dry particles contain 30 g of erythromycin.
Operating Method:

The compound with the highest melting point in a thermostat controlled receptacle is heated to 2° C. above its melting temperature, and the different compounds are then added gradually, in order of their melting point, from the highest melting point to the lowest melting point. The mix temperature is gradually reduced to be kept at 2° C. to 3° C. above the melting temperature of the new mix obtained. The erythromycine is added last. These compounds are dispersed in the lipidic phase using a stiffing system equipped with a mobile in a form of an anchor at a speed of 200 rpm. When the mix is homogenous, it is added to 600 ml of aqueous gel with 0.2% of Ultrez 10 carbopol, neutralised to pH 6.5 with soda, previously adjusted to the same temperature as the lipidic mix and contained in a reaction vessel equipped with a stiffing system with a three-vaned impeller. The stirring speed of the three-vaned impeller is 110 rpm during addition of the composition. Stirring is maintained for 30 seconds after the composition has been added and is then stopped. The dispersion is then cooled to 15° C. The particles are recovered by and then washed with distilled water, then with a mix of distilled water 5 with 15% of ethanol, and are then recovered and dried. The average size of the particles thus obtained is 62 microns. These particles have no active constituent on their surface.

After extraction, the erythromycin on the particles is analysed by HPLC. 29.3 g of erythromycin is obtained per 100 g of matrix.

It is well known that compositions containing erythromycin have a strong taste. The active constituent was not detected during the taste test carried out on the particles.

EXAMPLE 2

Preparation of a Syrup Containing Particles Containing Erythromycin

A pharmaceutical saccharose syrup distributed by the Cooper company and called Simple Syrup is used, with the following composition:

| | |
|---|---|
| Saccharose | 86.50 g |
| Sodium methyl parahydroxybenzoate | 0.15 g |
| Sodium propyl parahydroxybenzoate | 0.03 g |
| Pure water | to make 100 ml |

20 g of particles containing erythromycin obtained in example 1 are added to 250 ml of syrup at ambient temperature, corresponding to 5.86 g of erythromycin.

The active constituent was not detected during the taste concealing test carried out on the syrup.

EXAMPLE 3

Preparation of a Powder for Hydrodispersible Oral Administration, Containing Particles Containing Erythromycin The following are placed in a powder mixer:

| | |
|---|---|
| Particles according to example 1 | 100 g |
| Aroma | 7 g |
| Aspartamine | 3 g |
| Xanthene gum | 1 g |

After mixing, the powder is distributed in 2.24 g individual sachets containing 500 mg of erythromycin. An aqueous dispersion of the antibiotic is reconstituted by dissolution in 50 ml water. The active constituent was not detected during the taste test carried out on the dispersion.

EXAMPLE 4

Particles Containing Paracetamol

Example given for the production of 100 g of particles to reduce the gastrotoxicity of paracetamol:
Composition:

| | |
|---|---|
| Palm oil | 49.0 g |
| Oleic acid | 20.0 g |
| Stearic acid | 4.5 g |
| Capric acid | 1.0 g |
| Behenic acid | 0.5 g |
| Paracetamol | 25 g |

The operating method is exactly the same as that described in example 1.

The active constituent was not detected during the taste concealing test carried out on the particles.

EXAMPLE 5

Particles Containing Oxytetracycline

Example given for the preparation of 100 g of injectable particles with prolonged release and containing oxytetracycline:
Composition:

| | |
|---|---|
| Trilaurin | 39 g |
| Tricaprin | 32 g |
| Oleic acid | 3 g |
| Stearic acid | 1 g |
| Oxytetracycline | 25 g |

As mentioned in example 1, the particles were obtained by dispersion of the lipidic phase in the gelified aqueous phase while stiffing. The concentration of carbopol in the aqueous phase is 0.05%. Stirring is done using an axial turbo-stirring rod at a speed of 300 rpm, so as to reduce the average size of particles to 1 μm. Stirring is maintained for 60 seconds after the end of addition of the composition and is then stopped. The dispersion is then cooled to 15° C. The particles are recovered by sieving and are then washed with distilled water, and then by a mix of distilled water with 15% of ethanol, and are then recovered and dried. The average size of the particles thus obtained is 1.2 microns.

The invention claimed is:

1. A galenic system for oral administration in the form of strictly hydrophobic solid lipidic particles containing no water, surfactants, emulsifying agents or traces of solvents, characterised in that it comprises at least one hydrophobic wax, an active constituent, and additionally at least one non-neutralised fatty acid; wherein the hydrophobic solid lipidic particles have a melting temperature between 30° C. and 45° C. after incorporation of the active constituent.

2. The galenic system according to claim 1 characterised in that the lipidic particles are in a spherical form.

3. The galenic system according to claim 1, characterised in that the hydrophobic wax is a vegetable, animal or mineral wax, or a mix of at least one wax and at least one non-amphiphilic oil.

4. The galenic system according to claim 1, characterised in that quantity of the hydrophobic wax is between 0.5% and 99%.

5. The galenic system according to claim 1, characterised in that it also comprises at least one additional hydrophobic compound capable of adjusting the melting point and physicochemical properties of the galenic system.

6. The galenic system according to claim 1, characterised in that the melting point of the hydrophobic wax may be between 15 and 75° C.

7. The galenic system according to claim 1, characterised in that the hydrophobic wax is chosen from among triglycerides and derivatives, palm oil, Carnauba wax, Candellila wax, Alfa wax, cocoa butter, ozokerite, vegetable waxes, beeswaxes and modified beeswaxes.

8. The galenic system according to claim 1, characterised in that the non-neutralised fatty acid is chosen from among fatty acids with linear chains with between 4 and 18 carbon atoms and has a content by mass of between 0.5% and 75%.

9. The galenic system according to claim 1, characterised in that it is in the form of lipidic particles with a size of between 0.5 microns and 1500 microns.

10. The galenic system according to claim 1, characterised in that the capacity of particles for holding the active constituent ranges from 0.02% to 75% by weight of the particles.

11. A galenic system for oral administration in the form of strictly hydrophobic solid lipidic particles containing no water, surfactants, emulsifying agents or traces of solvents, characterised in that it comprises at least one hydrophobic wax having a melting point between 30° C. and 45° C. and additionally at least one non-neutralised fatty acid.

12. A galenic system for oral administration in the form of strictly hydrophobic solid lipidic particles containing no water, surfactants, emulsifying agents or traces of solvents, characterised in that it comprises at least one vegetable wax selected from olive wax, rice wax, hydrogenated jojoba wax or absolute flower waxes; and additionally at least one non-neutralised fatty acid.

13. The galenic system according to claim 11, characterised in that the lipidic particles are in a spherical form.

14. The galenic system according to claim 11, characterised in that the hydrophobic wax is a vegetable, animal or mineral wax, or a mix of at least one wax and at least one non-amphiphilic oil.

15. The galenic system according to claim 14, characterised in that the hydrophobic wax is chosen from among triglycerides and derivatives, palm oil, Carnauba wax, Candellila wax, Alfa wax, cocoa butter, ozokerite, vegetable waxes, beeswaxes and modified beeswaxes.

16. The galenic system according to claim 11, characterised in that quantity of the hydrophobic wax is between 0.5% and 99%.

17. The galenic system according to claim 11, characterised in that it also comprises at least one additional hydrophobic compound capable of adjusting the melting point and physicochemical properties of the galenic system.

18. The galenic system according to claim 11, characterised in that the non-neutralised fatty acid is chosen from among fatty acids with linear chains with between 4 and 18 carbon atoms and has a content by mass of between 0.5% and 75%.

19. The galenic system according to claim 11, characterised in that it is in the form of lipidic particles with a size of between 0.5 microns and 1500 microns.

* * * * *